United States Patent [19]
Thomas et al.

[11] Patent Number: 5,764,402
[45] Date of Patent: Jun. 9, 1998

[54] OPTICAL CELL CONTROL SYSTEM

[75] Inventors: Jean-François Thomas, Braine-le-Château, Belgium; Pierre Vezin, Bures/Yvette, France

[73] Assignee: Glaverbel, Brussels, Belgium

[21] Appl. No.: 737,011

[22] PCT Filed: Apr. 24, 1995

[86] PCT No.: PCT/BE95/00040
§ 371 Date: Oct. 28, 1996
§ 102(e) Date: Oct. 28, 1996

[87] PCT Pub. No.: WO95/30172
PCT Pub. Date: Nov. 9, 1995

[30] Foreign Application Priority Data

Apr. 29, 1994 [GB] United Kingdom ............... 9408603

[51] Int. Cl.$^6$ ............... G02F 1/03; G02F 1/15; H01L 41/04
[52] U.S. Cl. ............... 359/272; 359/265; 359/268; 359/275; 359/245; 349/33; 310/321
[58] Field of Search ............... 359/265–275, 359/245; 345/87, 98, 105, 204, 211; 310/317, 321; 349/33

[56] References Cited

U.S. PATENT DOCUMENTS 3,991,416 11/1976 Byles et al. .................. 345/87
4,212,513 7/1980 Gravel ...................... 310/317
5,189,547 2/1993 Day et al. ................... 359/245

FOREIGN PATENT DOCUMENTS 2366958 5/1978 France.
2190516 11/1987 United Kingdom.
90/07381 7/1990 WIPO.

*Primary Examiner*—David C. Nelms
*Assistant Examiner*—Evelyn A. Lester
*Attorney, Agent, or Firm*—Spencer & Frank

[57] ABSTRACT

A control system for an optical cell (light valve) is provided which comprises a first (oscillator) circuit supplied by a low voltage power source and including a primary winding of an induction coil and a secondary (resonant) circuit which includes the optical cell and a secondary winding of the induction coil. The secondary circuit includes the inductance of the secondary winding and the optical cell, and the induction coil provides a weak coupling between the primary and secondary windings. The resonant circuit provides a large over-voltage coefficient and great stability and the configuration made possible by the invention facilitates a significant reduction in the bulk of the control system.

27 Claims, 1 Drawing Sheet

OPTICAL CELL CONTROL SYSTEM

This invention relates to a control system for an optical cell (also called a light valve).

An optical cell may be formed by sandwiching a layer of sensitive material between two parallel plates of rigid, generally transparent sheet material, each plate having an electrically conducting surface layer facing the sensitive material. Examples of constituents of the sensitive material include suspended particles, liquid crystals and a layer of electrochromic material.

By applying or not applying an electric potential across the facing plates the constituents can be switched between a state in which light can pass and a state in which light is absorbed, scattered or reflected.

Optical cells, including optical cells having a control system according to the invention, can be used in mirrors or in glazing panels for vehicles or buildings so as to provide variable light transmission. For example they can be used as a glazing panel adjustable between an opaque and clear condition to limit solar transmission or to conceal the interior of a room or vehicle to provide privacy therein. They can be used in a vehicle sun-visor or sunshine roof panel or on an aircraft porthole.

The control system of the invention is particularly well suited for use with an optical cell used in a rear-view mirror of a motor vehicle, and is described herein largely with reference to that application.

The use of an optical cell in a rear view mirror is known for example from French patent specification FR 2 366 958 (Brisard Gerard) so as to provide a rear-view device in which the reflectivity varies as a function of the degree of dazzle. Traditional vehicle rear-view mirrors with an anti-dazzle feature, often called "prismatic" mirrors, have a "day" position and a "night" position, the mirror position being changed manually by the vehicle driver between the day and night positions. In the day position the degree of luminous reflectivity from a rear-view mirror is required to be high, generally greater than 50%. In the night position the reflectivity is limited to 12% or less, often about 4%, in order to avoid dazzling of the driver by fights such as the headlights of following vehicles.

Optical cells offer a rear-view mirror with the possibility of automatic adjustment according to the incident light conditions, adjusting from day to night positions and vice versa and to intermediate variations between those limits, thereby giving advantages in terms of convenience and safety. The cell is located adjacent and parallel to the reflective surface of the mirror and in the line of sight between the reflective surface and the vehicle driver. The cell thus provides a variable level of light reflection from the mirror to the driver. In one preferred configuration the reflective layer is provided by one of the electrically conducting layers being a material which is also reflective.

The level of light transmission or reflection through the optical cell is adjusted by the control system, which is activated by the external conditions. The control system is desirably housed alongside the optical cell so as to form a combined unit therewith. Traditional control systems have however been of a bulk which has made for difficulties in miniaturising any unit of which they have formed a part.

An object of the present invention is to provide a control system for an optical cell which can be conveniently accommodated adjacent to the cell.

According to the invention there is provided a control system for an optical cell, which system comprises a first circuit supplied by a low voltage power source and including an oscillator and a primary winding of an induction coil and further comprises a secondary circuit which includes the optical cell and a secondary winding of the aforementioned induction coil, characterised in that the secondary circuit is a resonant circuit which includes the inductance of the secondary winding and the optical cell, and the induction coil provides a weak coupling between the primary and secondary windings.

The control system of the invention thus uses the inductance of the secondary winding of the coil as the inductance of a resonant (oscillating) circuit. The configuration made possible by the invention facilitates a significant reduction in the bulk of the control system.

A particular advantage of the system according to the invention is that high voltages are confined to the secondary circuit, thereby providing a system with a reduced number of components subjected to high voltages. Since high voltages can create problems of safety and electromagnetic interference, the limitation of high voltage to the secondary circuit is beneficial in reducing the space occupied by high voltage components and in reducing the amount of protective casing required to enclose them.

Several different types of optical cell are known. These include an electrochromic optical cell or a liquid crystal optical cell or an electrodeposition optical cell. In electrodeposition the passage of a current through a transparent liquid containing a metallic salt causes the migration of metallic ions to the surface of the glass and the formation of a metallic coating which absorbs the light. The electrodes in this case are $SnO_2$ coatings. Liquid crystal optical cells, electrodeposition optical cells and electrochromic optical cells are generally transparent at rest but in certain conditions, such as the presence of an over-voltage or a prolonged period in an excited state, the return to a state of clarity from an excited state may take some time, even a matter of hours, and thus the switching speed of the cell may be relatively slow.

The preferred type of optical cell for use with the control system of the invention incorporates a fluid suspension of dispersed minute particles capable of orientation by an electrical field to change the transmission of light through the suspension, such as described, for example, in United States patent U.S. Pat. No. 3,655,267 (Research Frontiers). These optical cells switch rapidly from a clear state to a dark state. They also provide a wide range of luminosity. Fluid suspensions of herapathite in a suitable liquid such as iso-pentyl acetate are preferred, although other types of particles can be used, such as graphite, mica, garnet red, aluminium and periodides of alkaloid sulphate salts.

The plates of transparent material forming an optical cell are typically located at a substantially uniform distance of about 50 µm from each other across the whole of their facing areas. If this distance is not maintained within a tolerance of, for example, about 5 to 10 µm the transparency of the cell is not uniform and problems may also arise in short circuiting of the electrical field between two adjacent points on the opposing faces. This uniform-distance requirement imposes certain limits on the material from which the plates can be formed. Thus although plastic materials such as polyethylene terephthalate can be considered, difficulties may occur in maintaining the constant spacing between the sheets of plastics material over the whole surface of the cell. In general it is therefore preferred to employ glass sheets.

The faces of the plates facing each other in the cell are coated with an electrically conducting material. The preferred coating material is indium tin oxide (ITO), which is both conductive and transparent. The mirror surface of the rear view mirror of which the cell may form a part can conveniently be provided by a reflective layer of the face of one of the cell plates opposite to the electrically-coated face. The material for any such reflective coating on the plates is usually silver, chromium or aluminium.

When the cell forms part of a vehicle rear-view mirror, the reflective mirror surface and the cell are located in a housing attached to the vehicle, for example on the vehicle windscreen or a door. The circuit for controlling the adjustment of the optical cell is positioned in or on the housing. Electrical connectors are also provided in or on the housing to connect the optical cell to the electrical system of the vehicle.

In the control system according to the invention the optical cell is preferably connected directly to the secondary winding and the induction coil provides substantially all of the inductance of the secondary (resonant) circuit. This parallel resonant circuit provides a greater over-voltage coefficient and greater stability than a series circuit. The fact that the induction coil provides substantially the whole of the inductance of the resonant circuit ensures a slight bulk for the control system.

The term "weak coupling" is used herein, with reference to the magnetic coupling between the primary and secondary coil windings, to mean a coupling akin to that of a transformer but differing in that inductance leakage is deliberately increased. The coupling coefficient K can be calculated by the formula:

$$K = \frac{M}{\sqrt{L_p \cdot L_s}}$$

in which $L_p$ is the inductance of the primary winding, $L_s$ is the inductance of the secondary winding and M is the mutual inductance. For the purposes of the invention the coil should preferably have a coupling coefficient of less than 0.7, most preferably less than 0.5.

The coupling should be weak so as to reduce the influence of the primary circuit on the impedance of the secondary circuit, while being sufficient to transfer the energy necessary to initiate and maintain the resonance in the secondary circuit. Thus the energy is introduced by the bias of the coil, while avoiding disturbance to the characteristics of the secondary circuit The coil according to the invention is thus not constructed as a true transformer, in which as strong a coupling as possible is generally required, and instead functions as a poor transformer. The "weak coupling" coil of the invention does not have the purpose of a true transformer to transfer energy with the smallest possible losses.

The magnetic core of the induction coil is preferably constructed to provide a magnetic resistance to the passage of flux in the magnetic circuit which it forms. This is conveniently achieved by including a gap in the path of the lines of magnetic flux through the magnetic core. The gap is formed of a non-magnetic material, for example air or more usually a resin or plastic material. The size of the gap in the magnetic core is preferably at least 0.1 mm, most preferably at least 0.2 mm.

The secondary circuit provides the reactive energy to activate the optical cell. The operational frequency of the system can be imposed by the secondary circuit itself, in that the impulses in the system are continuously and automatically adjusted to the resonant frequency of the secondary circuit This is preferably achieved by constructing the electrical circuit in such a way that the secondary (resonant) circuit is an element which acts directly on the oscillating circuit and thus itself imposes the operational frequency.

In the case of a cell with a suspension of electrically orientable particles the frequency is typically of the order of 8 to 25 kHz, often in the range 16 to 25 kHz. The use of such alternating current avoids migration of suspended particles across the narrow distance between the adjacent plates, which migration would adversely affect the uniform opacity or clarity required from the cell. The frequency should be chosen to avoid audible frequencies.

In a system in which the frequency is imposed by the oscillator in the primary circuit, but not in the case of an auto-oscillating circuit, the frequency must be initially adjusted to the resonant frequency determined by the set-up of the cell circuit for each cell.

The control system of the invention offers the advantage that only a small amount of energy is needed to sustain the required resonance. A specific further advantage of the system according to the invention is that if the cell is broken the current may be retained within the circuit but with a much lower voltage.

The coil comprises a conventional core, typically of soft iron. The size of the core is preferably such as to fit within the housing of a rear-view mirror including the optical cell, the core being located behind the mirror relative to the vehicle driver.

The primary and secondary windings of the coil preferably do not overlap each other. Thus the primary winding is preferably formed around one portion of the core and the secondary winding around another portion of the core. This non-overlapping configuration also assists in providing the weak coupling between the windings and is of further benefit in making the system sufficiently small to fit into the mirror housing.

The primary winding preferably comprises less than 100 turns around the core, more preferably 10 to 80 turns and most preferably 40 to 80 turns. The secondary winding typically comprises 140 to 300 turns. The winding (transformation) ratio is thus typically of the order of 3 to 4:1. The main factor in achieving the required voltage across the cell is, however, not the winding ratio but rather the over-voltage in the secondary circuit. The said over-voltage is a function of the capacity, the inductance and the resistance of the elements which constitute the secondary circuit. The ability to use the over-voltage in the secondary circuit to achieve the required voltage across the cell is a particular advantage of the invention.

The wave form in the secondary circuit is substantially sinusoidal, even if the wave form of the impulses generated by the oscillator is not. The conversion of a non-sinusoidal wave (for example a square wave) generated by the oscillator into a sinusoidal wave in the secondary circuit is facilitated by the weak magnetic coupling in the induction coil. The voltage applied across the optical cell can be controlled by adjustment of the quantity of energy emitted by the oscillator in modulating the size of pulse, for example by changing its duration, or alternatively can be controlled by adjustment of the voltage peaks in the primary circuit.

The system preferably includes one or more feedback lines from the secondary circuit to the first circuit. This offers the advantage of adjusting the oscillator in response to the electrical parameters found on the optical cell.

Thus a feedback line can be provided to regulate the voltage in the secondary circuit and thereby to ensure at all times the required voltage across the optical cell for a required level of darkening of the cell. Alternatively or in addition the or a feedback line can also regulate the frequency acting on the oscillator frequency in the first circuit to ensure at all times the operational frequency of the secondary circuit at the resonant frequency thereof.

A reactive loop can be created which detects whether the operational frequency of the secondary circuit is truly the resonant frequency of the secondary circuit and sends any required correcting signal to the oscillator in the primary circuit to adjust its frequency so as to obtain resonance in the secondary circuit.

If the operational frequency is not the same as the resonant frequency of the secondary circuit, the over-voltage is lower and the active energy consumption is increased. To obtain good operations it is therefore advantageous to ensure that the operational frequency is equal to the resonant frequency, although control of the difference between the operational frequency and the resonant frequency may also, to some extent, control the voltage applied to the cell by controlling the over-voltage factor.

In one embodiment of the invention the secondary circuit includes at least one capacitor in parallel with the optical cell. In general it is preferred to employ two or more such capacitors in series with each other. The use of capacitors in series has the advantage of reducing the voltage applied across each individual capacitor.

The control system of the invention is applicable to a variety of different types of optical cell. The control system regulates the provision to the optical cell of an alternating current supply. For a cell with suspended orientable particles a voltage of up to about 125 V may be required, the voltage is applied between the conductive surfaces of the cell to generate an electrical field which orients the particles in a manner to allow the passage of light. In order to vary the luminous reflectivity or transmissivity of the optical cell, it is sufficient to vary the current voltage applied to the optical cell. One may also vary the frequency, but this is less efficient. The variation in luminosity is largely proportional to the applied voltage, up to a saturation limit In the absence of an electrical field, the particles are subject to Brownian movement and thus restrict the passage of light through the cell. In the presence of a weak field, the particles tend to align with the field but continue to oscillate about their mean position such that some light absorption light occurs. It is necessary to reach a certain threshold value for the electrical field, for example corresponding to a voltage of about 100 V, in order for the particles to be substantially fully aligned in the field and thus for minimum absorption of light to occur.

The control system is preferably regulated by at least one photosensitive optical device which detects the incident light falling on the optical cell. Advantageously, at least two such light detection devices are employed, the first being positioned to monitor potentially dazzling light coming from the rear of the vehicle and the second being positioned to monitor the ambient light level, for example the light coming through the windscreen, light reflected by the roof of the vehicle or light diffused by a transparent roof of the vehicle.

The control relies on the principle that a signal proportional to the light level detected by the photo-sensitive optical device, or on the difference in light levels detected by two such devices, is employed to act upon the oscillator in the primary circuit so as to adjust the voltage applied across the terminals of the optical cell, and thus the opacity of the cell.

Where, in addition to an internal rear-view mirror, one or more exterior rear-view mirrors are provided, the transmissivity and/or the reflectivity characteristics of the external rear-view assembly may be controlled by the same electronic circuit provided for the control of the internal rear-view assembly, to provide simultaneous adjustment of the transmissivity and/or reflectivity characteristics. However, because of the scope for miniaturisation and the small power consumption of control systems according to the invention, it is possible to include a separate control system in each of the mirrors. With such separate systems each of the mirrors is thereby adjusted according to the specific light conditions falling upon it.

The invention is further described below, by way of non-limiting example, with reference to the accompanying drawings, in which.

Figure 1:
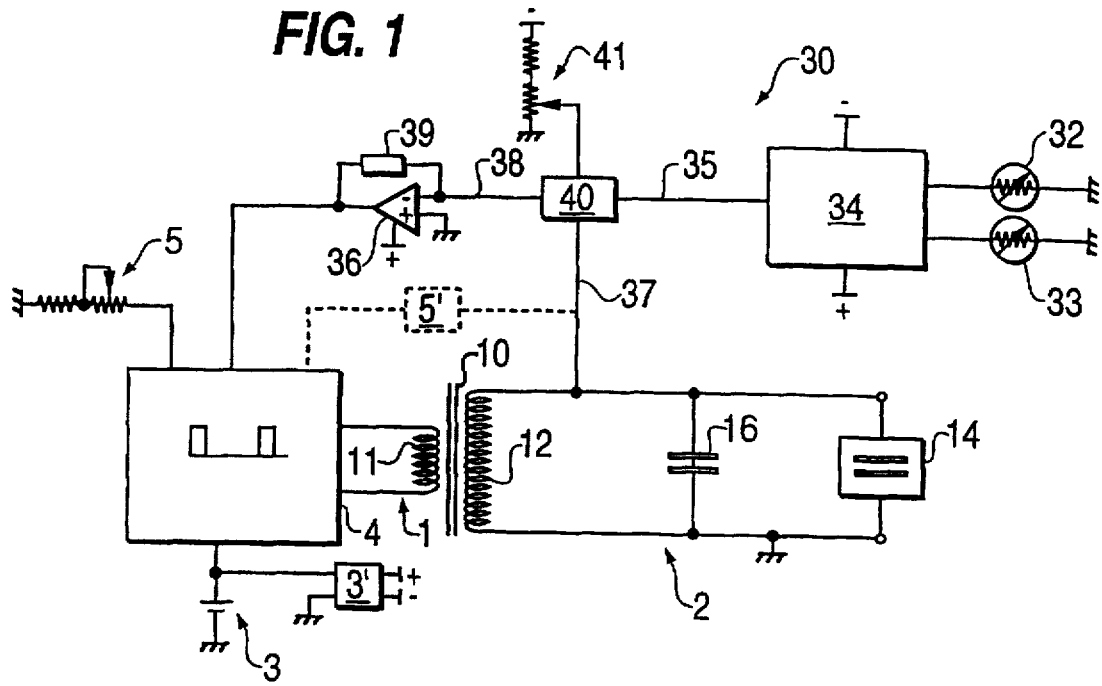
FIG. 1 is a circuit diagram of one version of control system according to the invention and intended for use in a motor vehicle.

The illustrated control system includes a first circuit 1 comprising a 12 volt DC battery 3, an oscillator 4 and a primary winding 11 of an induction coil having a magnetic core 10. The system further includes a secondary circuit 2 which includes the secondary winding 12 of the induction coil, an optical cell 14 and a capacitor 16 in parallel with the optical cell 14. The induction coil is shown diagrammatically in FIG. 1 and in greater detail in FIGS. 2 and 3.

The battery 3, which supplies low voltage power to the oscillator 4, is the electrical source for the whole of the electronic circuit. Apart from the battery 3 there is provision for components to impose negative and positive reference voltages upon certain parts of the circuit The first of these components is a DC—DC converter 3' in the line from the battery 3 to the oscillator 4.

The oscillator 4 has an associated actuation means 5, in this instance simply a potentiometer, which serves to adjust the frequency of the oscillator 4. In an alternative configuration the actuation means 5 is replaced by a frequency feedback means 5' (shown by dotted lines in FIG. 1) which detects the frequency in the secondary circuit and adjusts the oscillator 4 to this frequency. This alternative offers the benefit that the oscillator frequency is automatically adjusted to be always at the frequency of the secondary circuit The optical cell 14 is of the type which incorporates a liquid suspension of minute solid particles capable of orientation by an electric field. The capacitor 16 is preferably formed by four capacitors in series.

The system further includes a control circuit, indicated generally by the numeral 30, which includes two photoelectric light detection devices 32 and 33 linked to a detector control unit 34. A reference voltage is applied to the unit 34. A detector signal line 35 leads from the unit 34 to a signal comparison unit 40. The circuit 30 further includes an operational amplifier 36 with a feedback circuit 39. A cell-operation detector line 37 leads from the secondary circuit 2 to the comparison unit 40, from which a signal line 38 leads to the amplifier 36.

In the illustrated system the comparison unit 40 is also provided with an actuation means 41 (in this instance a potentiometer) to set a threshhold voltage. The means 41, which is not an essential component, serves to limit the voltage to a level sufficient for the proper functioning of the mirror while not subjecting the cell to a needlessly high voltage.

Figure 2:
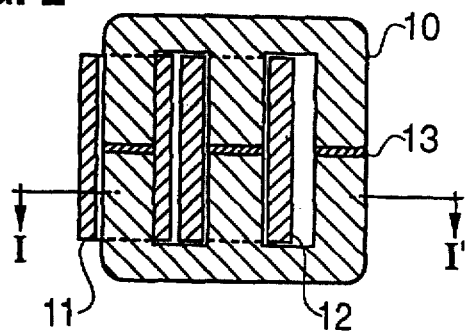
FIG. 2 is a sectional view of an induction coil used in the system.
Figure 3:
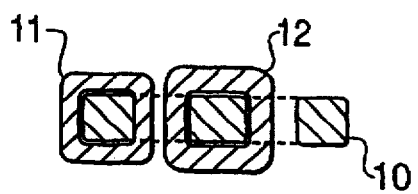
FIG. 3 is a different sectional view of the FIG. 2 induction coil, the section being taken along the line A—A' of FIG. 2.

The configuration of the induction coil used in the present example is shown in greater detail in the sectional views of FIGS. 2 and 3. The magnetic core 10 is formed of two facing E-shaped ferrites with a plastic spacer 13 between them. The spacer 13 provides resistance to the passage of flux in the magnetic circuit of the core 10. The secondary winding 12 is disposed around the central arm formed by the opposing central bars of the E-shaped ferrites, whereas the primary winding 11 is disposed around the opposing bars at one end of the ferrites.

The control system as a whole is mounted in a housing (not shown) and can be connected through the vehicle wiring harness to the 12 volt battery 3.

In use, the light detector 32 is positioned to detect the ambient light conditions, for example by capturing light from the front of the vehicle and/or light reflected by the roof, and the light detector 33 is positioned to detect light from the rear of the vehicle. The detector control unit 34 includes a difference detector which compares the signals from the light detectors 32 and 33 and feeds to line 35 a signal proportional in strength to the excess of the intensity of the rear-received light (33) over the ambient light (32). Any dazzling light impinging on the detector 33 sends a corresponding signal to the difference detector. The line 37 carries a signal proportional to the voltage of the secondary circuit 2. The signal sent by the control unit 34 via the line 35 is compared in the comparison unit 40 with the signal from the line 37 which indicates the secondary voltage and the comparison unit 40 in turn sends a control signal to the operational amplifier 36 via the line 38. This control signal takes into account the level of dazzle and the voltage actually applied across the optical cell. It would similarly be possible to include a further feedback means to provide a second control loop to feed back to the oscillator 4 the established frequency of the cell 14 (as shown in dotted lines by feedback means 5').

The signal from line 38 is amplified by the amplifier 36 to stimulate the oscillator 4 to generate a pulsed wave (although a sinusoidal wave or a square wave are possible variants) of low voltage AC in the primary circuit 1. This wave in turn induces through the coil a higher voltage in the secondary circuit 2 to be applied across the cell 14. The voltage across the cell 14 is further increased by the resonance in the secondary circuit and is typically up to about 120 volts AC, thus permitting the application to the cell 14 of a voltage to give partial or full alignment of its suspended particles. Full alignment provides the maximum light transmission through the cell 14 and thus the maximum reflectivity of the rear-view mirror of which the cell 14 forms a part.

If the ambient light detector 32 observes good daylight or a high level of artificial light and the rear-facing detector 33 observes similar conditions then the difference between the respective photo-electric signals is small and the unit 34 sends a signal via lines 35 and 38 and the amplifier 36 to activate the oscillator 4 and to generate a cell-activating voltage in the secondary circuit 2. The comparison unit 40 is informed via line 37 of the voltage actually produced in the secondary circuit and adjusts the command signal sent via line 38 so as to obtain the maximum voltage across the cell 14.

The oscillator 4 converts the 12 volt battery voltage to an AC voltage and a voltage of 120 volts AC is achieved in the secondary circuit 2. The AC frequency of the oscillator 4 is adjusted to the resonant frequency of the secondary circuit 2 by external action from the means 5 on the oscillator 4 and is normally about 20 kHz. This adjustment can be easily achieved by measuring the active current in the secondary circuit. When the frequency varies, the current follows a curve which passes through a minimum. The resonant frequency is achieved when the current is at the minimum.

This 120 volt maximum voltage in the secondary circuit 2 produces full alignment of the suspended particles in the cell 14.

As an alternative the frequency feedback means 5' provides a frequency control for the oscillator 4.

If the ambient light detector 32 observes dull or nighttime conditions and the rear-facing detector 33 observes similar conditions then the difference between the respective photo-electric signals is again small. The unit 34 again sends a signal via lines 35 and 38 and, as described above, again achieves the highest level of cell clarity and mirror reflectivity.

If, however, the ambient light detector 32 observes dull or nighttime conditions and the rear-facing detector 33 observes a dazzling full-beam headlight then the difference between the respective photo-electric signals is large and the unit 34 sends a corresponding signal to the amplifier 36. In this situation no voltage is produced in the induction coil 11/12 and no voltage in the cell 14. In the absence of a voltage in circuit 2 the cell particles adopt a random disposition, rendering the cell opaque and reducing the mirror reflectivity to its lowest level.

If the difference between the signals from the ambient light detector 32 and the rear-facing detector 33 lies between the extremes described above, for example in fairly dull conditions and with a mildly dazzling beam through the rear window, the unit 34 sends a signal via the amplifier 36 to the oscillator 4 which gives some stimulation of the oscillator 4 but the width of the pulses generated in circuit 1 is fairly narrow and thus the voltage in the secondary circuit 2 is correspondingly reduced. Under these conditions the secondary circuit voltage gives only partial alignment of the suspended particles in the cell 14, creating an intermediate level of opacity in the cell 14 and an intermediate level of reflectivity of the mirror as a whole.

If desired the ambient light detector 32 can be provided with a time delay component (not shown in the Figures) so that the cell 14 is not returned prematurely to the clear condition by the lights of a passing vehicle which briefly raise to a high level the ambient light reaching the detector 32.

In a typical example of a control system according to the invention the cell 14 had a capacity of 11 nF and the condenser 16, formed of four 22 nF condensers connected in series, thus had a capacity of 5.5 nF. Each E-shaped ferrite measured 25 mm (height)×13 mm (width)×8 mm (depth) and was made of material 3C8. The induction coil had 66 turns in the primary circuit (1) on one portion of the core, 240 turns in the secondary circuit (2) on another portion of the core, and a gap of 2.5 mm in the magnetic circuit. The primary winding 11 had an inductance $L_p$ of 0.318 mH, the secondary winding 12 had an inductance $L_s$ of 6.31 mH and the mutual inductance M was 0.6 mH. The coupling coefficient K of the induction coil, calculated by the formula quoted above, was 0.423.

In a variation of the above arrangement the secondary circuit can be part of an auto-oscillating circuit. In this alternative the secondary (resonant) circuit imposes the operational frequency on the oscillator.

We claim:

1. A control system of the reflexivity or transmissivity of an optical cell (14), which system comprises a first circuit (1) supplied by a low voltage power source (3) and including an oscillator (4) and a primary winding (11) of an induction coil and further comprises a secondary circuit (2) which includes the optical cell (14) and a secondary winding (12) of the aforementioned induction coil, the secondary circuit (2) being a resonant circuit, characterised in that said secondary circuit (2) includes the inductance of the secondary winding (12) and in that the magnetic circuit of the induction coil comprises a magnetic resistance to the passage of magnetic flux, to provide a weak coupling between the primary (11) and secondary (12) windings.

2. A control system as claimed in claim 1, in which the optical cell (14) is connected directly to the secondary winding (12) and the induction coil provides substantially all of the inductance of the resonant circuit (2).

3. A control system as claimed in claim 1, in which the induction coil comprises a magnetic core (10) which provides a magnetic resistance to the passage of flux in the magnetic circuit which it forms.

4. A control system as claimed in claim 3, in which the magnetic core (10) includes a gap (13) in the path of the lines of magnetic flux.

5. A control system as claimed in claim 4, in which the gap (13) in the magnetic core is at least 0.1 mm.

6. A control system as claimed in claim 5, in which the gap (13) in the magnetic core is at least 0.2 mm.

7. A control system as claimed in claim 1, in which the primary (11) and secondary (12) windings of the coil do not overlap each other.

8. A control system as claimed in claim 7, in which the primary winding (11) is formed around one portion of a magnetic core (10) and the secondary winding (12) is formed around another portion of the magnetic core (10).

9. A control system as claimed in claim 1, in which the primary winding (11) comprises less than 100 turns.

10. A control system as claimed in claim 9, in which the primary winding (11) comprises 10 to 80 turns.

11. A control system as claimed in claim 10, in which the primary winding (11) comprises 40 to 80 turns.

12. A control system as claimed in claim 1, in which the secondary winding (12) comprises 140 to 300 turns.

13. A control system as claimed in claim 1, in which the coupling coefficient of the induction coil is less than 0.7.

14. A control system as claimed in claim 13, in which the coupling coefficient of the induction coil is less than 0.5.

15. A control system as claimed in claim 1, in which the voltage across the optical cell (14) is adjusted by modulating the size of energy impulses applied to the primary winding (11).

16. A control system as claimed in claim 1, which includes at least one feedback line (5') from the secondary circuit (2) to the first circuit (1).

17. A control system as claimed in claim 16, in which the or a feedback line (5') regulates the voltage in the secondary circuit (2) to ensure at all times the required voltage across the optical cell (14) for a required level of darkening of the cell (14).

18. A control system as claimed in claim 16, in which the or a feedback line (5') regulates the frequency acting on the oscillator (4) frequency in the first circuit (1) to ensure at all times the operational frequency of the secondary circuit (2) at the resonant frequency thereof.

19. A control system as claimed in claim 1, in which the secondary circuit (2) includes at least one capacitor (16) in parallel with the optical cell (14).

20. A control system as claimed in claim 19, in which the secondary circuit (2) includes, in parallel with the optical cell (14), two or more capacitors (16) arranged in series with each other.

21. A control system as claimed in claim 1, in which the resonance of the secondary circuit (2) establishes the oscillation in the first circuit (1) and thereby determines the operational frequency of the system.

22. A control system as claimed in claim 1, which is regulated by at least one photo-sensitive optical device (32, 33) which detects the incident light falling on the optical cell (14).

23. A control system as claimed in claim 22, which includes two photo-sensitive optical devices (32, 33), one positioned to monitor potentially dazzling light coming from behind a vehicle and the other to monitor an ambient light level.

24. A control system as claimed in claim 1, in which the optical cell (14) is of the type which incorporates a fluid suspension of dispersed minute particles capable of orientation by an electrical field to change the transmission of light through the suspension.

25. A control system as claimed in claim 1, in which the optical cell is part of a rear-view mirror of a motor vehicle.

26. A control system as claimed in claim 25, which is located within a housing of the rear-view mirror.

27. A control system as claimed in claim 25, in which the induction coil comprises a core (10) which is sized to fit within a housing of the rear-view mirror.

* * * * *